(12) United States Patent
Fischer et al.

(10) Patent No.: US 6,992,226 B2
(45) Date of Patent: Jan. 31, 2006

(54) SINGLE-STAGE METHOD FOR PRODUCING TOLUENE DERIVATIVES

(75) Inventors: Rolf-Hartmuth Fischer, Heidelberg (DE); Markus Rösch, Oppenheim (DE); Norbert Götz, Worms (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/475,215

(22) PCT Filed: Apr. 24, 2002

(86) PCT No.: PCT/EP02/04486

§ 371 (c)(1),
(2), (4) Date: Oct. 20, 2003

(87) PCT Pub. No.: WO02/088046

PCT Pub. Date: Nov. 7, 2002

(65) Prior Publication Data

US 2004/0127752 A1    Jul. 1, 2004

(30) Foreign Application Priority Data

Apr. 27, 2001    (DE) ................ 101 20 911

(51) Int. Cl.
*C07C 41/18*    (2006.01)
(52) U.S. Cl. ...................... 568/648; 568/658
(58) Field of Classification Search ........... 568/628,
568/648, 650, 651, 652, 653, 772, 799, 658;
585/251, 267, 269, 270, 469
See application file for complete search history.

(56) References Cited

U.S. PATENT DOCUMENTS

| | | | |
|---|---|---|---|
| 2,355,219 A | 8/1944 | Ipatieff et al. | |
| 2,419,093 A | 4/1947 | Signaigo et al. | |
| 3,177,258 A * | 4/1965 | Koch, Jr. et al. | ........... 568/579 |

OTHER PUBLICATIONS

XP-002233768, Landa et al., 1322-1328, Collection of Czechoslovak Chemical Communication, vol. 23, 1958.
XP-002233769, Sugihara et al., 109-120.
XP-002233770 and Database WPI, Week 3081, Derwent Publication Ltd. JP56068635A.

* cited by examiner

*Primary Examiner*—Rosalynd Keys
(74) *Attorney, Agent, or Firm*—Novak Druce & Quigg LLP

(57) ABSTRACT

A process for preparing toluene derivatives of the formula I

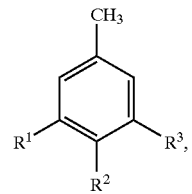

where $R^1$, $R^2$ and $R^3$ are, independently of one another, hydrogen, alkyl radicals, hydroxyl groups and/or alkoxy groups, comprises reacting the corresponding benzoic acids, benzoic esters or benzoic anhydrides with hydrogen in the presence of a catalyst.

13 Claims, No Drawings

SINGLE-STAGE METHOD FOR PRODUCING TOLUENE DERIVATIVES

The present invention relates to a process for preparing toluene derivatives by hydrogenation of benzoic acid and its derivatives, e.g. esters or anhydrides, by means of hydrogen in the presence of hydrogenation catalysts such as cobalt, nickel, ruthenium or palladium catalysts.

It is known that 3,4,5-trimethoxytoluene can be prepared by brominating p-cresol to form 3,5-dibromo-4-hydroxytoluene, reacting this compound with sodium methoxide to form 3,5-dimethoxy-4-hydroxytoluene and finally methylating the latter by means of dimethyl sulfate to give 3,4,5-trimethoxytoluene (J 5 6068-635, Nov. 12, 1979, Mitsui Petrochemical Ind.). A disadvantage of such a process is that the bromine used ends up in the form of an alkali metal bromide as coproduct.

If, for example, 3,4,5-trimethoxytoluene is to be prepared from gallic acid (3,4,5-trihydroxybenzoic acid) or gallic acid derivatives, the reduction of the carboxyl group (or corresponding ester group) to a methyl group has hitherto only been possible in two reaction steps:

Liebigs Annalen der Chemie, volume 763 (1972), pages 109–120, discloses initially hydrogenating alkyl esters of a 3,4,5-trialkoxybenzoic acid using lithium aluminum hydride to form a 3,4,5-trialkoxybenzyl alcohol which is then hydrogenated by means of hydrogen in glacial acetic acid as solvent in the presence of palladium-on-activated carbon catalysts to give the 3,4,5-trialkoxytoluene. Disadvantages are the two stages required and the formation of hydrated aluminum oxide as coproduct.

In Chemische Berichte, volume 99 (1966), pages 227–230, it is shown that 3,4,5-trimethoxybenzonitrile prepared from 3,4,5-trimethoxybenzoic acid or derivatives thereof can be reacted with terpenes as hydrogen donors in the presence of palladium on activated carbon as support to give 3,4,5-trimethoxytoluene. A disadvantage is, in particular, the formation of dehydrogenated terpenes and of ammonium salts as coproducts.

It is an object of the present invention to develop a single-stage process for the hydrogenation of unsubstituted or alkyl-, alkoxy- or hydroxy-substituted benzoic acids and their esters and anhydrides to form the corresponding toluene derivatives which proceeds in high yield and selectivity and without the formation of inorganic coproducts.

We have found that this object is achieved by a process for preparing toluene derivatives of the formula I

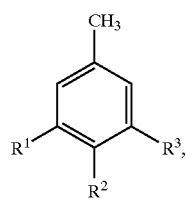

where $R^1$, $R^2$ und $R^3$ are, independently of one another, hydrogen, alkyl radicals having, for example, from one to six carbon atoms, hydroxyl groups and/or alkoxy groups of the formula —O—$R^4$, where $R^4$ is an alkyl radical having, for example, from one to six carbon atoms, which comprises reacting the corresponding benzoic acids, benzoic esters or benzoic anhydrides with hydrogen at an appropriate temperature and an appropriate pressure in the presence of homogeneous or heterogeneous catalysts.

It was surprisingly found that the reaction according to the present invention could be carried out in a single stage and with high yields and selectivities to the target products I.

The hydrogenation catalysts used according to the present invention preferably comprise (a) at least one metal and/or compound of a metal (for example metal oxides, nitrides or carbonates) selected from the group consisting of cobalt, nickel, ruthenium and/or palladium, and (b) from 0 to 30% by weight, based on the sum of the components (a)–(c), of each of one or more metals or compounds of metals selected from the group consisting of platinum, rhodium, iridium, osmium, copper, iron, silver, gold, chromium, molybdenum, tungsten, manganese, rhenium, zinc, cadmium, lead, aluminum, zirconium, tin, phosphorus, silicon, arsenic, antimony, bismuth and rare earth metals, and also (c) from 0 to 5% by weight, based on the sum of the components (a)–(c), of each of one or more compounds of alkali metals or alkaline earth metals, where the sum of the components (a) to (c) is 100% by weight.

One possible embodiment of the catalyst comprises (a) at least one metal and/or compound of a metal (for example metal oxides, nitrides or carbonates) selected from the group consisting of cobalt, nickel, ruthenium and/or palladium, and (b) from 0.1 to 30% by weight, based on the sum of the components (a)–(c), of each of one or more metals or compounds of metals selected from the group consisting of platinum, rhodium, iridium, osmium, copper, iron, silver, gold, chromium, molybdenum, tungsten, manganese, rhenium, zinc, cadmium, lead, aluminum, zirconium, tin, phosphorus, silicon, arsenic, antimony, bismuth and rare earth metals, and also (c) from 0.05 to 5% by weight, based on the sum of the components (a)–(c), of each of one or more compounds of alkali metals or alkaline earth metals.

Particularly preferred catalysts are ones in which the component (a) comprises at least one metal and/or compound of a metal selected from the group consisting of cobalt and nickel, in an amount of from 5 to 100% by weight each. Preference is also given to catalysts in which the component (a) comprises at least one metal and/or compound of a metal selected from the group consisting of ruthenium and palladium in an amount of from 5 to 100% by weight each, in each case based on the sum of the components (a) to (c).

Particularly preferred catalysts comprise as component (b) at least one metal or compound of a metal selected from the group consisting of silver, copper, molybdenum, manganese, rhenium, lead and phosphorus, in an amount of from 0 to 25% by weight each, based on the sum of the components (a) to (c).

Particularly preferred catalysts comprise as component (c) at least one compound of an alkali metal or alkaline earth metal selected from the group consisting of lithium, sodium, potassium, cesium, magnesium and calcium, in an amount of from 0 to 5% by weight each, based on the sum of the components (a) to (c).

Very particularly preferred catalysts comprise only component (a) and no components (b) and (c).

Particularly preferred catalysts comprise cobalt or a cobalt compound as component (a).

Preference is also given to catalysts which comprise palladium or a palladium compound as component (a).

As starting materials, it is possible to use, in particular, compounds of the formula II

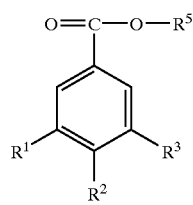

where $R^1$, $R^2$ and $R^3$ are as defined above and $R^5$ is hydrogen, an alkyl radical having, for example, from one to twelve carbon atoms, an aryl radical, a cycloalkyl radical, a heterocyclic radical or a radical —CO—$R^6$, where $R^6$ is an alkyl radical having, for example, from one to six carbon atoms.

If carboxylic anhydrides of the formula II with $R^5$=—CO—$R^6$ are used as starting materials, particular preference is given to catalysts comprising palladium or a palladium compound as component (a).

The catalysts can be used as homogeneous catalysts in dissolved form or as heterogeneous catalysts. Heterogeneous catalysts can be supported catalyts, all-active catalysts or Raney catalysts which are employed as a fixed bed, in suspended form or as a fluidized bed. Possible support materials are, for example, oxides such as aluminum oxide, silicon dioxide, aluminosilicates, lanthanum oxide, titanium dioxide, zirconium dioxide, magnesium oxide, zinc oxide and zeolites and also activated carbon or mixtures thereof.

The heterogeneous catalysts are generally produced by precipitating precursors of the component (a), optionally together with precursors of the component (b) (promoters) and/or optionally with precursors of the trace component (c) in the presence or absence of support materials (depending on the type of catalyst desired), optionally converting the catalyst precursor obtained in this way into extrudates or pellets, drying it and subsequently calcining it. Supported catalysts can generally also be obtained by impregnating the support with a solution of the components (a) and optionally (b) and/or (c), with the individual components being able to be added simultaneously or in succession, or by spraying the components (a) and optionally (b) and/or (c) onto the support using methods known per se. If necessary, binders can be used in the production of the catalysts.

Precursors used for the components (a) are generally readily water-soluble salts of the abovementioned metals, for example nitrates, chlorides, acetates, formates and sulfates, preferably nitrates.

Precursors used for the components (b) are generally readily water-soluble salts or complexes of the abovementioned metals, for example nitrates, chlorides, acetates, formates and sulfates, preferably nitrates.

Precursors used for the components (c) are generally readily water-soluble salts of the abovementioned alkali metals and alkaline earth metals, for example hydroxides, carbonates, nitrates, chlorides, acetates, formates and sulfates, preferably hydroxides and carbonates.

The precipitation is generally carried out from aqueous solutions, either by addition of precipitation reagents, by altering the pH or by altering the temperature.

The catalyst precursor composition obtained in this way is usually dried at from 80 to 150° C., preferably from 80 to 120° C.

The calcination is usually carried out at from 150 to 500° C., preferably from 200 to 450° C., in a stream of air or nitrogen.

If desired, the catalyst surface is passivated, usually by means of oxygen/nitrogen mixtures such as air at from 20 to 80° C., preferably from 25 to 35° C.

The calcined and, if desired, passivated catalyst composition obtained is generally exposed to a reducing atmosphere ("activation"), for example by exposing it to a gas stream comprising free hydrogen for from 2 to 60 h at from 80 to 250° C., preferably from 80 to 180° C., in the case of catalysts based on ruthenium or palladium and/or compounds of ruthenium or palladium as component (a), or at from 150 to 500° C., preferably from 180 to 400° C., in the case of catalysts based on one or more metals and/or compounds of metals selected from the group consisting of nickel and cobalt as component (a). The gas stream preferably consists of from 20 to 100% by volume of hydrogen and from 0 to 80% by volume of an inert gas such as nitrogen.

The fact that the catalyst is preferably activated directly within the synthesis reactor affords advantages in terms of process economics.

The hydrogenation can be carried out batchwise, but is preferably carried out continuously. In the case of continuous operation, it can be carried out in the upflow or downflow mode, in the gas phase or preferably in the liquid phase.

The starting materials II can be hydrogenated in bulk, e.g. as a melt, or else as a solution in a solvent.

Suitable solvents are ones which have sufficient solvent capability for the starting materials II and the target products I and are stable under the hydrogenation conditions. Examples of such solvents are ethers such as tetrahydrofuran, dioxane, tetrahydropyran, polyethylene glycol dialkyl ethers or polyethylene glycol monoalkyl ethers, alcohols such as methanol, ethanol, tert-butanol, cyclohexanol, water, carboxylic acids, phenols such as catechol, resorcinol, hydroquinone, pyrogallol and alkyl ethers of these phenols.

Preferred solvents are tetrahydrofuran, dioxane, tetrahydropyran, polyethylene glycol dialkyl ethers, polyethylene glycol monoalkyl ethers, water, acetic acid and propionic acid.

Particularly preferred solvents are water, ethers, in particular cyclic ethers and polyethylene glycol monoalkyl or dialkyl ethers.

The hydrogenation in the presence of palladium catalysts can also be carried out advantageously in carboxylic acids, e.g. $C_1$–$C_4$-carboxylic acids such as acetic acid or propionic acid.

The hydrogenation is, for example, carried out in a 1–60% strength by weight solution of the starting materials II in the abovementioned solvents.

The hydrogenation is advantageously carried out in the range from 20 to 260° C. at pressures of from 1 to 300 bar. In the presence of palladium or ruthenium catalysts, the hydrogenation is preferably carried out from 20 to 150° C. and pressures of from 1 to 150 bar. In the presence of nickel and cobalt catalysts, on the other hand, it is preferably carried out at from 100 to 260° C. and pressures of from 50 to 300 bar.

Preference is given to carrying out the hydrogenation at elevated pressures.

The hydrogen used for the hydrogenation is generally employed in a relatively high stoichiometric excess relative to the starting compound II.

It can be recirculated to the reaction as circulating gas. The hydrogen is generally used in the form of pure industrial-grade hydrogen. However, the presence of significant amounts of inert gases, e.g. nitrogen, do not interfere with the reaction.

The compounds I which can be prepared by means of the hydrogenation of the present invention are valuable intermediates which can be used for producing pharmaceutical products, fine chemicals and crop protection agents.

The invention is illustrated below by means of examples.

Catalysts

Catalyst A: 100% Pd, as 10% of Pd on activated carbon (Sigma-Aldrich Chemie GmbH)

Catalyst B: 65.4% of CoO; 20.2% of CuO; 8.3% of $Mn_3O_4$; 3.5% of $MoO_3$; 2.4% of $P_2O_5$; 0.2% of $Na_2O$ Catalyst C: 74.0% of NiO; 2.2% of $MoO_3$; 23.8% of CuO; on $ZrO_2$ as support Activation of Catalysts B and C at Atmospheric Pressure After charging an electrically heatable reactor having a capacity of 1 liter with the catalyst, the temperature is increased from groom temperature to 290° C. at a rate of about 20° C. per hour while passing 300 l/h of nitrogen through the reactor. The nitrogen is then replaced by hydrogen over a period of 6 hours. For this purpose, the proportion of hydrogen is increased by 50 l/h every hour and at the same time the proportion of nitrogen is decreased by 50 l/h every hour. When 300 l/h of hydrogen are being fed in, the reactor temperature is increased to 300–310° C. and maintained at this level for 48 hours while passing 300 l/h of hydrogen through the reactor. After cooling under argon, the catalyst is taken out and can be stored under tetraethylene glycol dimethyl ether.

Preparation of Toluene Derivatives of the Formula I

EXAMPLE 1

5.22 g of 3,4,5-trimethoxybenzoic acid derivative II ($R^1$, $R^2$, $R^3$=$OCH_3$; $R^5$=—CO—$R^6$; $R^6$=$OC_2H_5$) are dissolved in 30 ml of glacial acetic acid and introduced together with 0.62 g of catalyst A into a 50 ml autoclave. The autoclave is pressurized with 120 bar of hydrogen at room temperature. Further hydrogen is introduced at regular intervals until the pressure remains constant. The autoclave is subsequently vented, and the product is found to comprise 81% of 3,4,5-trimethoxytoluene and 4% of 3,4,5-trimethoxybenzoic acid.

EXAMPLE 2

20 g of 3,4,5-trimethoxybenzoic acid are dissolved in 130 ml of tetraethylene glycol dimethyl ether and introduced together with 5 g of the activated catalyst B into an autoclave. After flushing the autoclave a number of times with hydrogen, it is pressurized at room temperature with 50 bar of hydrogen, the contents of the autoclave are heated to 180° C. and the hydrogen pressure is increased to 200 bar. Further hydrogen is introduced at regular intervals until the pressure remains constant. The conversion is found to be 97% and 74.6% of 3,4,5-trimethoxytoluene are found in the product.

EXAMPLE 3

10 g of 3,4,5-trimethoxybenzoic acid are dissolved in 130 ml of tetrahydrofuran and introduced together with 2.5 g of the activated catalyst B into an autoclave. After flushing the autoclave a number of times with hydrogen, it is pressurized at room temperature with 50 bar of hydrogen, the contents of the autoclave are heated to 180° C. and the hydrogen pressure is increased to 200 bar. Further hydrogen is introduced at regular intervals until the pressure remains constant. The conversion is found to be 73.2% and 48.6% of 3,4,5-trimethoxytoluene are found in the product.

EXAMPLE 4

2 g of 3,4,5-trimethoxybenzoic acid are dissolved in 130 ml of water and introduced together with 1 g of the activated catalyst C into an autoclave. After flushing the autoclave a number of times with hydrogen, it is pressurized at room temperature with 50 bar of hydrogen, the contents of the autoclave are heated to 180° C. and the hydrogen pressure is increased to 200 bar. Further hydrogen is introduced at regular intervals until the pressure remains constant. The conversion is found to be 68% and 53.3% of 3,4,5-trimethoxytoluene are found in the product.

We claim:

1. A process wherein 3,4,5-trimethoxytoluene is prepared in a single stage by reacting a benzoic acid, benzoic ester or benzoic anhydride corresponding to 3,4,5-trimethoxytoluene with hydrogen in the presence of a catalyst comprising
   (a) at least one metal and/or compound of a metal selected from the group consisting of cobalt, nickel, ruthenium and/or palladium, and
   (b) from 0 to 30% by weight, based on the sum of the components (a)–(c), of each of one or more metals or compounds of metals selected from the group consisting of platinum, rhodium, iridium, osmium, copper, iron, silver, gold, chromium, molybdenum, tungsten, manganese, rhenium, zinc, cadmium, lead, aluminum, zirconium, tin, phosphorus, silicon, arsenic, antimony, bismuth and rare earth metals, and also
   (c) from 0 to 5% by weight, based on the sum of the components (a)–(c), of each of one or more compounds of alkali metals or alkaline earth metals,
   where the sum of the components a) to c) is 100% by weight.

2. A process as claimed in claim 1, wherein the catalyst comprises as component (a) at least one metal and/or compound of a metal selected from the group consisting of cobalt and nickel, in an amount of from 5 to 100% by weight each.

3. A process as claimed in claim 1, wherein the catalyst comprises as component (a) at least one metal and/or compound of a metal selected from the group consisting of ruthenium and palladium in an amount of from 5 to 100% by weight each, in each case based on the sum of the components (a) to (c).

4. A process as claimed in claim 1, wherein the catalyst comprises as component (b) a metal or a compound of a metal selected from the group consisting of silver, copper, molybdenum, manganese, rhenium, lead and phosphorus.

5. A process as claimed in claim 1, wherein the catalyst comprises as component (c) a compound of an alkali metal or alkaline earth metal selected from the group consisting of lithium, sodium, potassium, cesium, magnesium and calcium.

6. A process as claimed in claim 1, wherein the catalyst comprises cobalt or a cobalt compound as component (a).

7. A process as claimed in claim 1, wherein a catalyst comprising palladium or a palladium compound as component (a) is used when benzoic anhydrides are employed as starting compounds.

8. A process as claimed in claim 1, wherein the hydrogenation is carried out in the liquid phase.

9. A process as claimed in claim 1, wherein the hydrogenation is carried out in a solvent selected from among tetrahydrofuran, dioxane, tetrahydropyran, polyethylene glycol dialkyl ethers, polyethylene glycol monoalkyl ethers, methanol, ethanol, tert-butanol, cyclohexanol, water, carboxylic acids, the phenols catechol, resorcinol, hydroquinone, pyrogallol and alkyl ethers of these phenols.

10. A process as claimed in claim 1, wherein the hydrogenation is carried out in a solvent selected from among tetrahydrofuran, dioxane, tetrahydropyran, polyethylene glycol diethers, polyethylene glycol monoethers, water, acetic acid and propionic acid.

11. A process as claimed in claim 1, wherein the hydrogenation is carried out at from 20 to 260° C. and pressures of from 1 to 300 bar.

12. A process as claimed in claim 1, wherein the hydrogenation is carried out at from 100 to 260° C. and pressures of from 50 to 300 bar in the presence of a catalyst comprising nickel or cobalt as component (a).

13. A process as claimed in claim 1, wherein the hydrogenation is carried out at from 20 to 150° C. and pressures of from 1 to 150 bar in the presence of a catalyst comprising palladium or ruthenium as component (a).

* * * * *